(12) United States Patent
Christesen

(10) Patent No.: US 6,875,241 B2
(45) Date of Patent: Apr. 5, 2005

(54) VARIABLE RESISTANCE CELL

(75) Inventor: Roland J. Christesen, Fayette, UT (US)

(73) Assignee: Roland J. Christesen, as Operating Manager of RJC Development LC, General Partner of the Roland J. Christensen Family Limited Partnership, Fayette, UT (US)

( * ) Notice: Subject to any disclaimer, the term of this patent is extended or adjusted under 35 U.S.C. 154(b) by 0 days.

(21) Appl. No.: 10/360,261

(22) Filed: Feb. 5, 2003

(65) Prior Publication Data
US 2003/0120353 A1 Jun. 26, 2003

Related U.S. Application Data

(63) Continuation-in-part of application No. 10/137,933, filed on May 3, 2002, now Pat. No. 6,663,673, which is a continuation-in-part of application No. 09/607,494, filed on Jun. 30, 2000, now abandoned.

(51) Int. Cl.⁷ .................................................. A61F 2/66
(52) U.S. Cl. .................... 623/56; 188/267.1; 188/267.2
(58) Field of Search ........................ 623/56; 267/140.14, 267/140.15; 188/372, 267, 267.1, 267.2

(56) References Cited

U.S. PATENT DOCUMENTS

| | | |
|---|---|---|
| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,779,765 A | 10/1930 | Eichhorn |
| 1,996,874 A | 4/1935 | Mascau |
| 2,036,830 A | 4/1936 | Rowley |
| 2,379,538 A | 7/1945 | Meierhofer |
| 2,443,356 A | 6/1948 | Mathis |
| 2,453,969 A | 11/1948 | Carter |
| 2,470,480 A | 5/1949 | Fogg |
| 2,570,735 A | 10/1951 | Weise |

(Continued)

FOREIGN PATENT DOCUMENTS

| | | |
|---|---|---|
| DE | 295807 | 12/1916 |
| GB | 1191633 | 5/1970 |
| GB | 1550658 | 11/1976 |
| IT | 556381 | 2/1957 |
| RU | 560606 | 6/1977 |
| RU | 2033772 | 4/1995 |

Primary Examiner—Bruce E Snow
(74) Attorney, Agent, or Firm—Thorpe North & Western

(57) ABSTRACT

A variable resistance cell and method provides a variable resistance response to a load factor, such as a load, a load rate, a strain, a strain rate, a pressure, or a deflection. A variable viscosity fluid is displacable between first and second chambers of an enclosure though an orifice in response to the load factor. The variable viscosity fluid has a viscosity that is variable corresponding to the load factor to vary an ability of the variable viscosity fluid to flow through the orifice. The variable viscosity fluid can be a shear stiffening material that increases in viscosity with an increase in a load factor applied to the shear stiffening material, a magneto rheologic fluid responsive to a magnetic field, or an electro rheologic fluid responsive to an electric field. The enclosure can be compressible between first and second positions. In the first position, the cell is responsive to a relatively larger load factor and has a first larger dimension in which a lesser amount of the variable viscosity fluid passes through the orifice into the second chamber. In the second position, the cell is responsive to a relatively smaller load factor and has a second smaller dimension in which a greater amount of the variable viscosity fluid passes through the orifice into the second chamber 32 Claims, 4 Drawing Sheets

U.S. PATENT DOCUMENTS

| | | | |
|---|---|---|---|
| 2,617,115 | A | 11/1952 | Ellery |
| 2,640,200 | A | 6/1953 | Wisbrun |
| 2,843,853 | A | 7/1958 | Mauch |
| 3,551,914 | A | 1/1971 | Woodall |
| 3,871,032 | A | 3/1975 | Karas |
| 3,874,004 | A | 4/1975 | May |
| 3,906,552 | A | 9/1975 | Weber |
| 3,920,610 | A | 11/1975 | Wagner |
| 3,956,775 | A | 5/1976 | Moore |
| 3,982,280 | A | 9/1976 | Asbelle et al. |
| 4,089,072 | A | 5/1978 | Glabiszewski |
| 4,328,594 | A | 5/1982 | Campbell et al. |
| 4,506,395 | A | 3/1985 | Haupt |
| 4,547,913 | A | 10/1985 | Phillips |
| 4,645,509 | A | 2/1987 | Poggi et al. |
| 4,676,801 | A | 6/1987 | Lundeen |
| 4,721,510 | A | 1/1988 | Cooper et al. |
| 4,822,363 | A | 4/1989 | Phillips |
| 4,865,611 | A | 9/1989 | Al-Turaiki |
| 4,938,775 | A | 7/1990 | Morgan |
| 4,959,073 | A | 9/1990 | Merlette |
| 5,019,109 | A | 5/1991 | Voisin |
| 5,030,239 | A | 7/1991 | Copes |
| 5,037,444 | A | 8/1991 | Phillips |
| 5,112,356 | A | 5/1992 | Harris et al. |
| 5,116,383 | A | 5/1992 | Shorter et al. |
| 5,116,384 | A | 5/1992 | Wilson et al. |
| 5,181,932 | A | 1/1993 | Phillips |
| 5,181,933 | A | 1/1993 | Phillips |
| 5,217,500 | A | 6/1993 | Phillips |
| 5,267,633 | A * | 12/1993 | Endo et al. .............. 188/267.1 |
| 5,290,319 | A | 3/1994 | Phillips |
| 5,376,133 | A | 12/1994 | Gramnäs |
| 5,376,141 | A | 12/1994 | Phillips |
| 5,387,246 | A | 2/1995 | Phillips |
| 5,425,781 | A | 6/1995 | Allard et al. |
| 5,425,782 | A | 6/1995 | Phillips |
| 5,443,528 | A | 8/1995 | Allen |
| 5,443,529 | A | 8/1995 | Phillips |
| 5,458,656 | A | 10/1995 | Phillips |
| 5,464,441 | A | 11/1995 | Phillips |
| 5,482,513 | A | 1/1996 | Wilson |
| 5,486,209 | A | 1/1996 | Phillips |
| 5,507,838 | A | 4/1996 | Chen |
| 5,509,936 | A | 4/1996 | Rappoport et al. |
| 5,509,938 | A | 4/1996 | Phillips |
| 5,514,185 | A | 5/1996 | Phillips |
| 5,514,186 | A | 5/1996 | Phillips |
| 5,549,714 | A | 8/1996 | Phillips |
| 5,571,210 | A | 11/1996 | Lindh |
| 5,571,213 | A | 11/1996 | Allen |
| 5,593,455 | A | 1/1997 | Phillips |
| 5,593,456 | A | 1/1997 | Merlette |
| 5,593,457 | A | 1/1997 | Phillips |
| 5,653,767 | A | 8/1997 | Allen et al. |
| 5,725,598 | A | 3/1998 | Phillips |
| 5,728,175 | A | 3/1998 | Rincoe |
| 5,728,176 | A | 3/1998 | Phillips |
| 5,728,177 | A | 3/1998 | Phillips |
| 5,766,265 | A | 6/1998 | Phillips |
| 5,769,896 | A | 6/1998 | Rosendahl et al. |
| 5,776,205 | A | 7/1998 | Phillips |
| 5,779,735 | A | 7/1998 | Molino |
| 5,800,565 | A | 9/1998 | Biedermann |
| 5,800,569 | A | 9/1998 | Phillips |
| 5,824,112 | A | 10/1998 | Phillips |
| 5,888,238 | A | 3/1999 | Phillips et al. |
| 5,893,891 | A | 4/1999 | Zahedi |
| 5,899,944 | A | 5/1999 | Phillips |
| 5,944,760 | A | 8/1999 | Christensen |
| 5,976,191 | A | 11/1999 | Phillips |
| 5,993,488 | A | 11/1999 | Phillips |
| 6,019,795 | A | 2/2000 | Phillips |
| 6,071,313 | A | 6/2000 | Phillips |
| 6,120,547 | A | 9/2000 | Christensen |
| 6,165,227 | A | 12/2000 | Phillips |
| 6,197,068 | B1 | 3/2001 | Christensen |
| 6,206,934 | B1 | 3/2001 | Phillips |
| 6,241,776 | B1 | 6/2001 | Christensen |
| 6,254,643 | B1 | 7/2001 | Phillips |
| 6,261,324 | B1 | 7/2001 | Merlette |
| 6,280,479 | B1 | 8/2001 | Phillips |
| 6,290,730 | B1 | 9/2001 | Pitkin et al. |
| 6,443,993 | B1 * | 9/2002 | Koniuk .................. 623/24 |
| 6,663,673 | B2 * | 12/2003 | Christensen ............ 623/56 |

\* cited by examiner

VARIABLE RESISTANCE CELL

This application is a continuation-in-part of U.S. patent application Ser. No. 10/137,933, filed May 3, 2002, now U.S. Pat. No. 6,663,673 which is a continuation-in-part of U.S. patent application Ser. No. 09/607,494, filed Jun. 30, 2000, now abandoned.

BACKGROUND OF THE INVENTION

1. Field of the Invention

The present invention relates generally to a variable resistance cell and method that provides a variable resistance response to a load factor.

2. Related Art

It is desirable in various situations to provide a variable resistance in response to an applied condition, such as a load. For example, such a situation can include prosthetic feet, and the applied condition can include static forces, such as the weight of the amputee, dynamic forces such as impact loads during use. In addition, it is often desirable to provide greater resistance to greater applied conditions, and lesser resistance to lesser applied conditions. For example, under normal use conditions, it is desirable for a prosthetic foot to have a softer, more cushioned feel, while under strenuous use conditions, it is desirable for the prosthetic foot to have a harder feel. In addition, it can be desirable or necessary to vary the resistance or performance of the prosthetic foot due to other conditions, such as changes in weight.

SUMMARY OF THE INVENTION

It has been recognized that it would be advantageous to develop a variable resistance cell to provide a variable resistance response to a load factor. In addition, it has been recognized that it would be advantageous to develop such a cell that displaces or compresses a lesser amount in response to a greater load factor, but that displaces or compresses a greater amount in response to a lesser load factor.

The invention provides a variable resistance cell to provide a variable resistance response to a load factor. The cell can include an enclosure with first and second chambers. An orifice can be operatively disposed between the first and second chambers, and sized to provide resistance against fluid flow therethrough. A variable viscosity fluid is disposed in the enclosure and is displacable between the first and second chambers though the orifice in response to the load factor. The variable viscosity fluid has a viscosity that is variable corresponding to the load factor to vary an ability of the variable viscosity fluid to flow through the orifice. The enclosure is compressible between first and second positions. In the first position, the cell responds to a relatively larger load factor and has a first larger dimension in which a lesser amount of the variable viscosity fluid passes through the orifice into the second chamber. In the second position, the cell responds to a relatively smaller load factor and has a second smaller dimension in which a greater amount of the variable viscosity fluid passes through the orifice into the second chamber. The load factor can include a force, a load, a load rate, a strain, a strain rate, a pressure, a pressure rate, a deflection, a deflection rate, or an acceleration of any of the previous. The viscosity of the fluid can be varied in either chamber, and/or the orifice.

In accordance with a more detailed aspect of the present invention, the cell can be biased to the first position. The cell can include a spring coupled to the enclosure to bias the enclosure to the first position. In addition, the enclosure can be resilient and biased to the first position.

In accordance with another more detailed aspect of the present invention, the enclosure can be flexible. The enclosure can flex outwardly in the second position to form the second chamber. The enclosure can include a tubular sleeve.

In accordance with another more detailed aspect of the present invention, the cell can include means for varying the viscosity of the variable viscosity fluid in response to the load factor.

In accordance with another more detailed aspect of the present invention, the variable viscosity fluid can include a shear stiffening material that increases in viscosity with an increase in the load factor applied to the shear stiffening material. In addition, the variable viscosity fluid can include a magneto rheologic fluid responsive to a magnetic field, or an electro rheologic fluid responsive to an electric field. A transducer can be used to sense a load factor. A power source and control electronics can be coupled to the transducer and the variable viscosity fluid to apply an electric or magnetic field in response to the load factor sensed by the transducer. The control electronics can be programmed to respond to the load factor and provide a desired control signal.

In accordance with another more detailed aspect of the present invention, a block can be disposed in the enclosure to divide the enclosure into the first and second chambers, and to form the orifice between the block and the enclosure. A cup can be formed around the first chamber to receive the block therein in the second position. The block and the cup include a magnetic material.

In accordance with another more detailed aspect of the present invention, the cell can include a variable orifice with a variable size.

In accordance with another more detailed aspect of the present invention, one or more cells can be disposed between first and second members of a prosthetic foot. The cells can be arranged to resist movement in for and aft directions (or planter flexion and dorsal flexion), and/or in side-to-side directions (or inversion and eversion). In addition, the cell can be disposed in a shoe between upper and lower surfaces of an outsole.

A method for variably resisting a load factor can include displacing a variable viscosity fluid through a variable resistance cell. The cell can include an enclosure with two chambers and an orifice positioned between the two chambers so that the variable viscosity fluid can flow between the two chambers through the orifice. The variable resistance load cell can be compressed by applying a load factor to the variable resistance cell. The viscosity of the fluid can be varied in response to the load factor by increasing the viscosity for a relatively larger load factor, and decreasing the viscosity for a relatively smaller load factor. In addition, the resistance can be programmed, such as in control electronics.

Additional features and advantages of the invention will be apparent from the detailed description which follows, taken in conjunction with the accompanying drawings, which together illustrate, by way of example, features of the invention.

DETAILED DESCRIPTION

Figure 1:
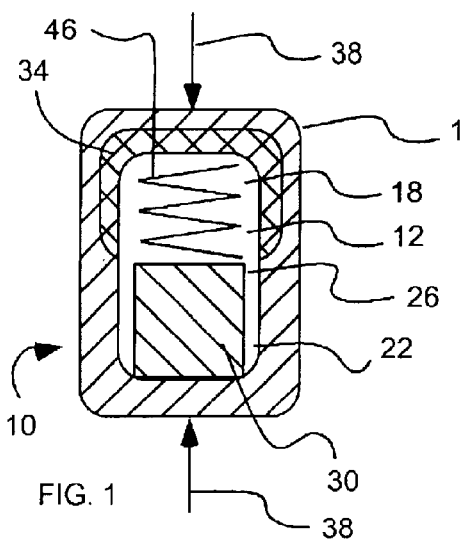
FIG. 1 is a cross-sectional side view of a variable resistance cell in accordance with an embodiment of the present invention, shown under a relatively larger load factor.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 2:
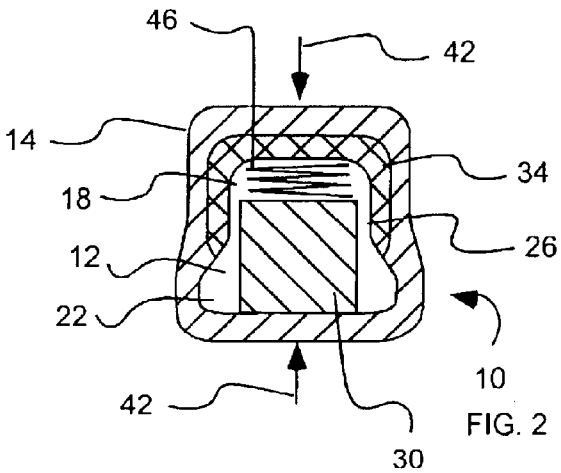
FIG. 2 is a cross-sectional side view of the variable resistance cell of FIG. 1, shown under a relatively smaller load factor.

As illustrated in FIGS. 1 and 2, a variable resistance cell or device, indicated generally at 10, in accordance with the present invention is shown for providing a variable resistance in response to an applied load factor. Such a variable resistance cell 10 can be used is such applications as prosthetic feet and shoes. The variable resistance cell 10 advantageously allows the stiffness or response of the prosthetic feet or shoes to be varied. The variable resistance cell can increase in stiffness, and/or decrease in displacement, with an increase in a load factor applied to the cell. Such load factors can include a load, a load rate, a strain, a strain rate, a pressure, a pressure rate, a deflection, a deflection rate, an acceleration of any of the preceding, etc.

The variable resistance cell 10 advantageously can include a variable viscosity fluid or material 12. The variable viscosity fluid can increase in viscosity with an increase in a load factor applied to the variable viscosity fluid. As described in greater detail below, the variable viscosity fluid or material can include a shear stiffening material that increases in viscosity as a load or strain, or load rate or strain rate, is applied; an electro rheologic fluid that changes viscosity under an applied electric field; or a magneto rheologic fluid that changes viscosity under an applied magnetic field.

The cell 10 can include an enclosure 14 with first and second chambers or reservoirs 18 and 22. The variable viscosity fluid 12 is disposed in the enclosure 14, and is displaceable between the first and second chambers 18 and 22. The cell 10 or enclosure 14 can include a tubular sleeve closed at opposite ends to form the enclosure. The sleeve can include a tubular wall, and the enclosure, sleeve or wall can be flexible, or formed of a flexible material. The enclosure or sleeve can be generally cylindrical, and can be divided into the first and second chambers.

An orifice 26 can be positioned in the cell 10 or enclosure 14, and operatively disposed between the first and second chambers 18 and 22. The variable viscosity fluid 12 can flow or be displaced through the orifice 26. Thus, the fluid 12 is displaceable between the chambers 18 and 22 through the orifice 26. The orifice 26 is sized to provide resistance against the flow of fluid through the orifice. The orifice 26 can have an annular shape. A block 30 can be disposed in the enclosure 14, and can divide the enclosure into the first and second chambers 18 and 22. In addition, the block 30 can form the orifice 26 between the block and the enclosure. The block and the enclosure or sleeve can be cylindrical, forming an annular orifice. The block can be disposed in the second chamber 22, or in one end of the enclosure, such as a lower end. The block can be formed of a flexible and resilient material, and can be substantially solid, as shown, or can be hollow. The block can be flexible to deflect under load, but can be more rigid relative to the enclosure or sleeve.

A cup 34 can be disposed in the first chamber 18, or in another end of the enclosure, such as an upper end. In addition, the cup 34 can be formed around the first chamber, and sized and shaped to receive the block 30. Like the block 30, the cup 34 can be formed of a flexible and resilient material, and can be flexible to deflect under load, but can be more rigid relative to the enclosure or sleeve.

As described above, the variable viscosity fluid 12 is displacable between the first and second chambers 18 and 22 though the orifice 26 in response to the load factor. The variable viscosity fluid 12 has a viscosity that is variable corresponding to the load factor. The variation in viscosity of the load factor varies an ability of the variable viscosity fluid to flow through the orifice 26. The viscosity of the fluid 12 advantageously can be selectively varied to vary the flow of the fluid through the orifice 26, and between the chambers 14 and 18. The viscosity of the fluid can be varied in either chamber, and/or the orifice.

As described above, the cell 10 and enclosure 14 can be flexible and compressible. In use, the enclosure 14 can be compressible and expandable between different positions, as shown in FIGS. 1 and 2. The enclosure 14 can expand to a first or expanded position, as shown in FIG. 1, and compress to a second or compressed position, as shown in FIG. 2. In the first position, the cell 10 or enclosure 14 responds to a relatively larger load factor, indicated by arrows 38. In addition, in the first position, the cell 10 and enclosure 14 have a first larger dimension or thickness, and a lesser amount or volume of the variable viscosity fluid 12 passes from the first enclosure 18, through the orifice 26 and into the second chamber 22. Thus, the cell 10 provides less displacement and a stiffer feel in response to the larger load factor 38. In the second position, the cell 10 or enclosure 14 responds to a relatively smaller load factor, indicated by arrows 42. In addition, in the second position, the cell 10 has a second smaller dimension or thickness, and a greater amount or volume of the variable viscosity fluid 12 passes from the first chamber 18, through the orifice 26 and into the second chamber 22. Thus, the cell 10 provides a greater displacement and a softer feel in response to the smaller load factor 42.

As a load factor is applied to the cell 10, the fluid 12 displaces from the first chamber 18 to the second chamber 22 through the orifice 26. As the load factor increases, the viscosity of the fluid 12 also increases, and less fluid flows through the orifice 26, resulting in less displacement or compression of the enclosure 12, and a rigid feel. As the load factor decreases, the viscosity of the fluid 12 also decreases, and more fluid flows through the orifice 26, resulting in more displacement or compression of the enclosure 12, and a softer feel.

As described above, the block 30 can be disposed in the second chamber 22, and the enclosure 14 can be flexible. In addition, as the enclosure 14 flexes or compresses in the second position, a portion of the enclosure flexes outwardly around the block 30 to further form the second chamber 22. The enclosure 14 or sleeve can expand outwardly.

In addition, as the cell 10 or enclosure 14 flexes or compresses, the cup 34 can be displaced towards the block 30 so that the block 30 is received in the cup 34 or into the first chamber 18. As described above, while the enclosure 14 or sleeve can be flexible, the cup 34 can be rigid, or more rigid, to maintain the shape of the cup 34, and thus the first chamber 18, during compression of the enclosure 14 so that the block 30 can pass into the cup 34 without interfering with the compression. Under extreme deflection or compression of the enclosure 14, an upper end of the enclosure or the cup can impart a portion of the load factor to the block 34. Thus, as described above, the block 34 may be flexible, and can act as a stopper or further cushion.

The enclosure 14 or sleeve can be resilient, or can be formed of a resilient material, so that the enclosure or sleeve tends to retain its shape, or is biased to the first position, without loading. In addition, the cell 10 can include a biasing member coupled to the enclosure and biasing the enclosure to the first position. The biasing member can include a spring 46 disposed in the enclosure 14 or first chamber 18. The spring 46 can extend between the block 30 and the cup 34, and can exert a force to separate the block and cup. The spring, or course, compresses as the load factor is applied to the cell.

The variable viscosity fluid 12 can include a shear stiffening material that increases in viscosity with an increase in the load factor applied to the shear stiffening material. An example of such shear stiffening material is a composition of cornstarch and water. Under little or no load factor (indicated by arrows 42), the shear stiffening material can be less viscous and capable of greater flow, and thus can be displacable while the cell can be compressible, as shown in FIG. 2. Under greater load factor (indicated by arrows 38), the shear stiffening material can be more viscous and less capable of flowing, and thus can be less displacable while the cell can be less compressible, as shown in FIG. 1. It will be appreciated that the less-viscous shear stiffening material dissipates more energy or force. Similarly, the more-viscous shear stiffening material transfers more energy or force. The shear stiffening material is one example of means for varying the viscosity of the variable viscosity fluid in response to the load factor.

Figure 3:
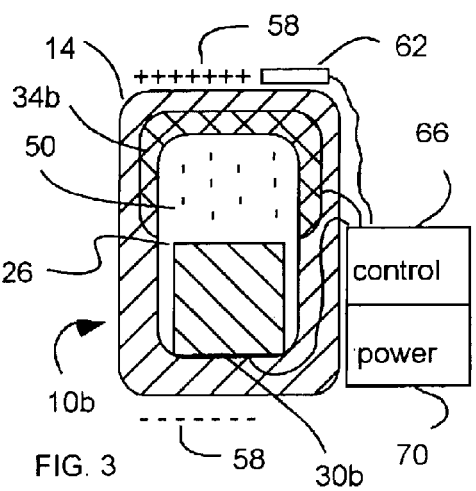
FIG. 3 is a cross-sectional side view of another variable resistance cell in accordance with an embodiment of the present invention, shown under a relatively larger load factor.
Figure 4:
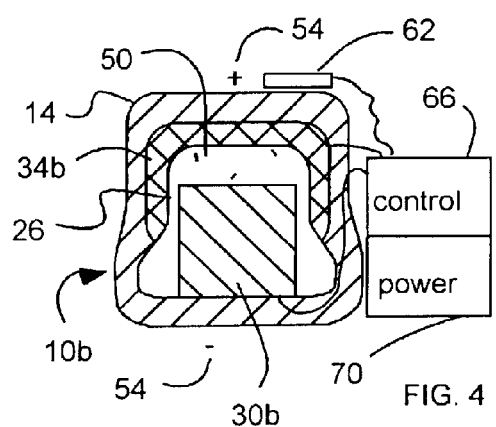
FIG. 4 is a cross-sectional side view of the variable resistance cell of FIG. 3, shown under a relatively smaller load factor.

Referring to FIGS. 3 and 4, another variable resistance cell 10b is shown that is similar in many respects to the one described above, but the variable viscosity fluid or material 12 can include an electro rheologic fluid 50 that is responsive to an applied electric field to alter its viscosity. Such an electro rheologic fluid 50 increases in viscosity as an electric field is applied. Under little or no electric field (indicated at 54 in FIG. 4), the electro rheologic fluid 50 can be less viscous and capable of greater flow, and thus can be displacable, as shown in FIG. 4. Under a greater electric field (indicated at 58 in FIG. 3), the electro rheologic fluid 50 can be more viscous and less capable of flowing, and thus can be less displacable, as shown in FIG. 3.

A transducer 62, such as a strain gauge, can be associated with the cell 10b. The transducer 62 can be coupled to or disposed on the cell 10b, as shown, or can be located remote from the cell, such as on a prosthetic foot or shoe. The transducer 62 can sense strain or force, or another load factor, applied to the cell 10b, or to the foot or shoe. The transducer 62 can be operatively coupled to control electronics 66 and a power source 70. The control electronics 66 and transducer 62 can be operatively coupled to the electro rheologic fluid 50, such as by electrodes coupled to the enclosure. For example, the block 30b and cup 34b can be electrodes, and can be operatively coupled to the control electronics 66, power source 70, and/or transducer 62. The control electronics 66 can include amplifier circuitry, while the power source 70 can be a battery. The transducer 62 can sense strain or force in the first and/or second members 18 and 22, and can produce a signal that can be sent to the control electronics 66.

The control electronics 66 can include amplifier circuitry to amplify the signal to create a control signal. The control electronics can create the control signal based on input from the load factors, or based on any other inputs. In addition, the control electronics 66 can be programmable, such as with a computer chip, to provide specific signals, or to modify the signals in a specific manner, to correspond to different applications or activities. For example, control electronics 66 can be provided with programs to provide or modify signals to correspond to different activities, such as walking or running when the cells are used with prosthetic feet or shoes. The control signal can be applied to the electro rheologic fluid 50 by the electrodes, such as the block 30b and the cup 34b. It will be appreciated that the control electronics 66 can include inputs to vary the amplification, minimums, etc., to control or customize the cell. The transducer can be coupled to the cell or enclosure containing the variable viscosity fluid. Thus, the transducer 62 can be configured to sense pressure of the variable viscosity fluid in the enclosure.

The electro rheologic fluid 50 can include particles or filings in an oil. As the electric field 58 is applied, the particles or filings align, increasing the viscosity of the fluid 50, or the oil with particles or filings. With no or little electrical field 54, the particles or filings are random, decreasing the viscosity of the fluid 50, or the oil with particles or filings. The electric field, power source, electrodes and/or particles or filings are examples of means for varying the viscosity of the variable viscosity fluid in response to the load factor.

Figure 5:
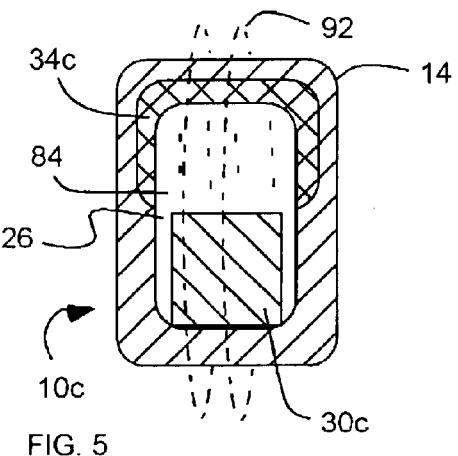
FIG. 5 is a cross-sectional side view of another variable resistance cell in accordance with an embodiment of the present invention, shown under a relatively larger load factor.
Figure 6:
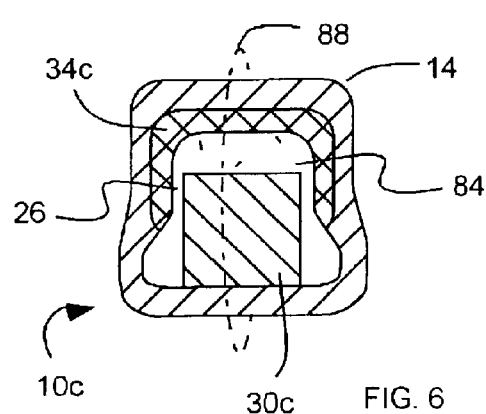
FIG. 6 is a cross-sectional side view of the variable resistance cell of FIG. 5, shown under a relatively smaller load factor.

Referring to FIGS. 5 and 6, another variable resistance cell 10c is shown that is similar in many respects to the one described above, but the variable viscosity fluid or material 12 can include a magneto rheologic fluid 84 that is responsive to an applied magnetic field to alter its viscosity. Such a magneto rheologic fluid 84 increases in viscosity as a magnetic field is applied. Under little or no magnetic field (represented by lines 88), the magneto rheologic fluid 84 can be less viscous and capable of greater flow, and thus can be displacable, as shown in FIG. 6. Under a greater magnetic field (represented by lines 92), the magneto rheologic fluid 84 can be more viscous and less capable of flowing, and thus can be less displacable, as shown in FIG. 5.

The magnetic field can be applied by magnets that are operatively coupled to the enclosure 14. For example, the block 30c and the cup 34c can be magnetic, or can include a magnetic material. In addition, the magnets can be electromagnets operatively coupled to control electronics, as described above with respect to FIGS. 3 and 4, using the control signal to generate the magnetic field. Such a magneto rheologic fluid 84 can include particles or filings in an oil. As the magnetic field 92 is applied, the particles or filings align, increasing the viscosity of the fluid, or the oil with particles or filings. With little or no magnetic field 88, the particles or filings are random, decreasing the viscosity of the fluid, or the oil with particles or filings. The magnetic field, magnets, and/or particles or filings are one example of means for varying the viscosity of the variable viscosity fluid in response to the load factor.

Figure 7:
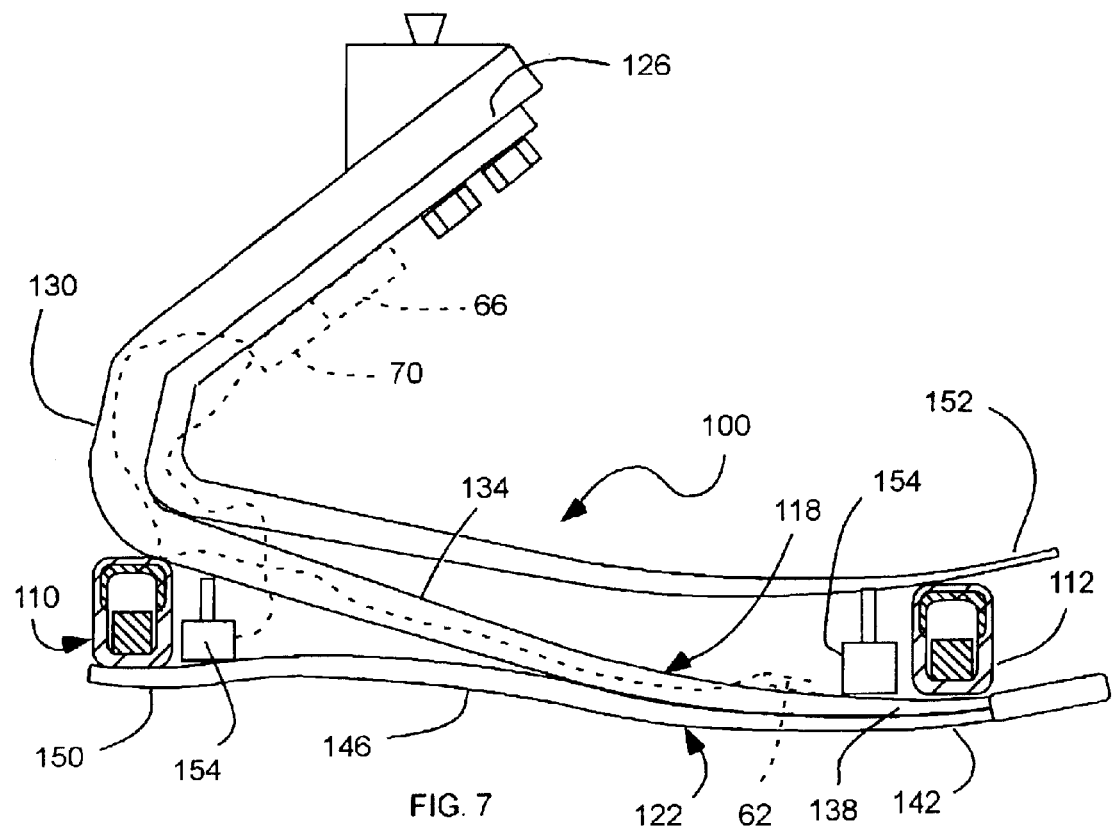
FIG. 7 is a side view of a prosthetic foot with a variable resistance cell in accordance with the present invention.

As stated above, variable resistance cells, such as those described above can be used with prosthetic feet and footwear. The cell or the enclosure 14 can be disposed between first and second members of a prosthetic foot. Referring to FIG. 7, a prosthetic foot 100 is shown with one or more variable resistance cells 110 and/or 112 for varying the stiffness or response of the foot. The foot 100 can include an upper forefoot member 118 coupled to a stump of an amputee, as is understood in the art, and a lower foot plate or heel member 122 coupled to the upper forefoot member 118, and positioned to operate between the upper forefoot member and the ground. The upper forefoot member 118 can extend from an attachment section 126, which is coupled to a stump of an amputee, downwardly and forwardly through an ankle section 130, an arch section 134 and to a toe section 138. The foot plate or heel member 122 can be a full-length sole that extends from a toe section 142, through an arch section 146, and to a heel section 150. The members 118 and 122 can be coupled at the toe sections 138 and 142. A gap or space can be formed between the members, or between the ankle section 130 and the heel section 150. The cell 110 can be disposed in the space between the first and second members. The first and second members can be the upper forefoot member and the lower footplate.

In addition, the foot 100 can include a reinforcement member 152, similar to, but spaced above, the upper forefoot member 118. The reinforcement member 152 can add reinforcement to the upper forefoot member. A cell 112 can be disposed between the reinforcement member 152 and upper forefoot member 118, or between the toe sections. The first and second members can be the reinforcement member and the upper forefoot member. The first and second members can be the upper forefoot member and the reinforcement member.

The heel section 150 of the second member 122 can be located at a heel location in a region near the rear of the foot device where the heel of a natural foot would be located. Similarly, the toe sections 138 and 142 are located at a toe location in a region near the front of the foot device where the toes of a natural foot would be located.

The members 118, 122 and 152 can be resilient and energy storing foot members that deflect or flex, storing energy, much like a leaf spring. Thus, the members can be formed of a flexible and resilient material that allows the foot members to deflect or flex. In one aspect, the members can be formed of a fiber reinforced resin material, such as a graphite-reinforced resin.

The cells 110 or 112 or the prosthetic foot 100 can include a generator 154 to produce energy, such as electricity, to power the control electronics, the electrical signal, magnets, and/or cells. For example, the generator 154 can include coils and magnets movable with respect to one another to produce electricity, as is known in the art. The movement of the foot or shoe can provide the movement to the generator. The generator can be electrically coupled to the control electronics and cell.

The transducer 62 can be operatively coupled to the foot 100, the upper forefoot member 118, the lower foot member 122 or the reinforcement member 152 to sense strain or deflection or other load factor of the foot or members. In addition, the control electronics 66 and power source 70 also can be coupled to the foot 100.

Figure 8:
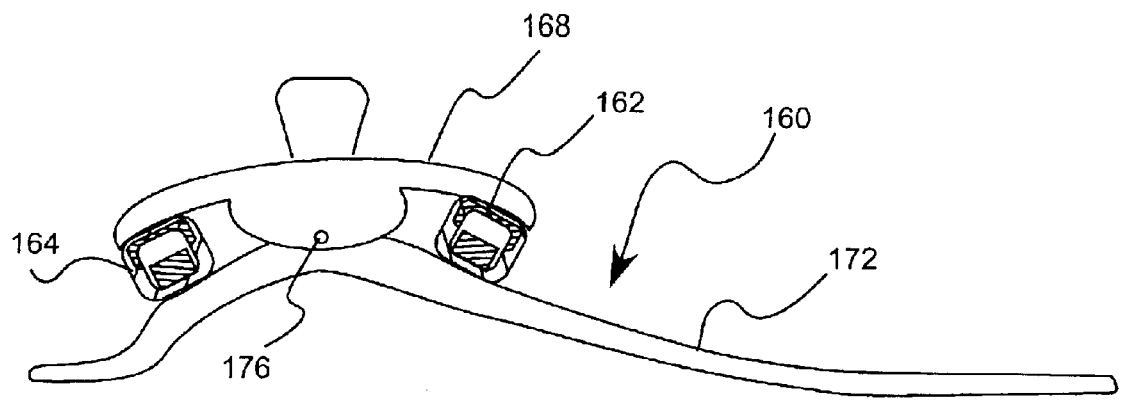
FIG. 8 is a side view of another prosthetic foot with a variable resistance cell in accordance with the present invention.

Referring to FIG. 8, another prosthetic foot 160 is shown with a pair of variable resistance cells 162 and 164. The prosthetic foot 160 can have a first member 168 to be coupled to a stump of an amputee, and a second member 172 pivotally coupled to the first member at a pivot point or pin 176. Spaces or gaps can be formed between the first and second members forward and rearward of the pivot point. The cells 162 and 164 can be disposed between the first and second members. As the second member 172 pivots about the pivot point 176 they apply force to the cells. The prosthetic foot 160 can include a generator, as described above and shown in FIG. 7.

Figure 9B:
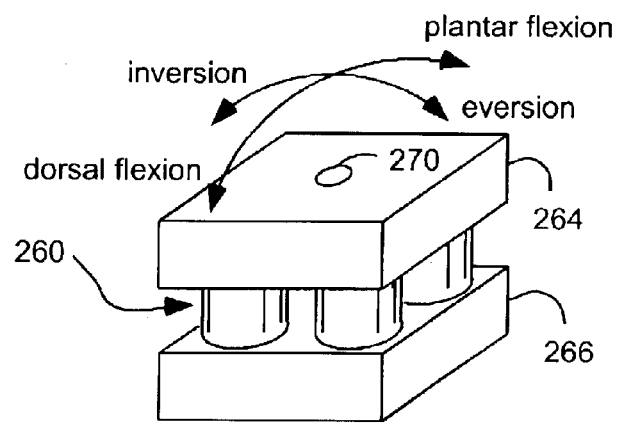
FIG. 9b is a perspective view of a portion of a prosthetic foot with variable resistance cells in accordance with the present invention.
Figure 9:
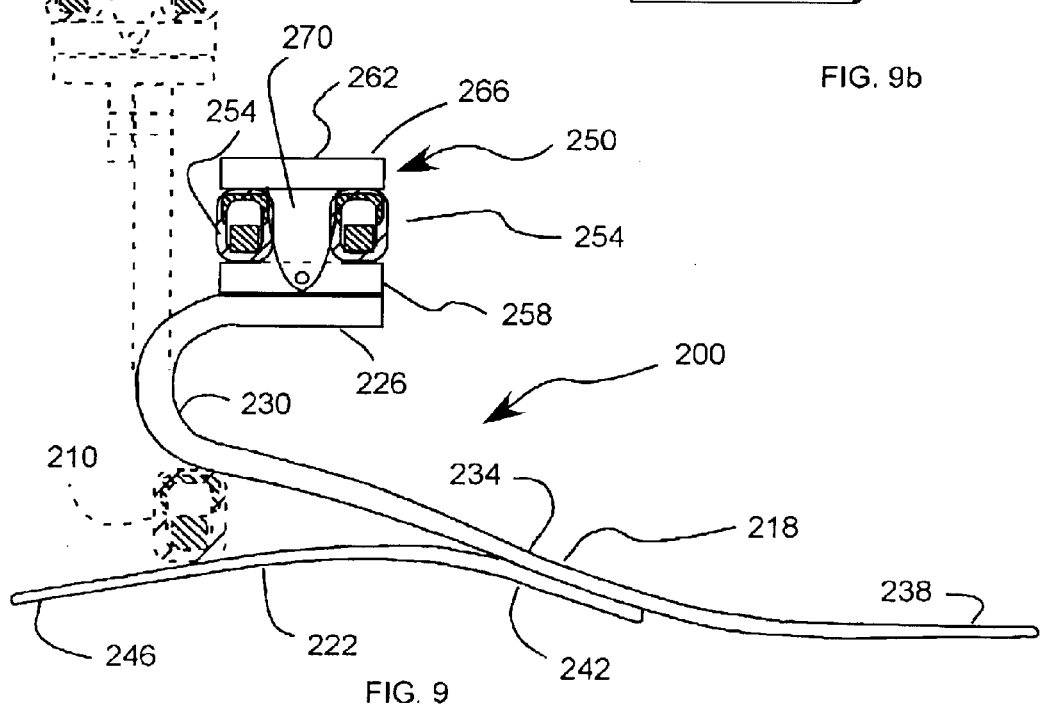
FIG. 9 is a side view of another prosthetic foot with a variable resistance cell in accordance with the present invention.

Referring to FIG. 9, another prosthetic foot 200 is shown with a variable resistance cell 210. The foot 200, however, has a different configuration than that described above. The foot 200 can have an upper or forefoot member 218 with an attachment section 226 (horizontal shown in solid lines, vertical shown in dashed lines), curving downwardly and forwardly through a curvilinear spring or ankle section 230, an arch section 234, and a toe section 238 at a toe location of toes of a natural foot. Thus, the upper of forefoot member 218 can have a general C-shape or a J-shape. In addition, the foot can have a lower heel member 222 with and can have an attachment section 242 attached to the arch section 234 of the upper or forefoot member 218, and extending rearwardly towards a heel section 246 at a heel location of a natural heel. The upper or forefoot member 218 can be a first member and the lower heel member 222 can be a second member. The variable resistance cell 210 can be disposed between the first and second members, or forefoot and heel members 218 and 222.

An adaptor 250 can be coupled to the prosthetic foot 200 such that the adaptor 250 forms the first member 322, and the prosthetic foot 200 forms the second member. A plurality of variable resistance cells 254 can be disposed between the adaptor 250 and the prosthetic foot 200. The adaptor 250 can attach in a horizontal manner to a horizontal attachment section of the prosthetic foot, as shown in solid lines, or in a vertical manner to a vertical attachment section of the prosthetic foot, as show in dashed lines. (It will of course be appreciated that the adaptor can be attached at any angle, and the horizontal and vertical are shown as typical attachments.)

The adaptor 250 can include an attachment plate 258 attached to the foot 200. The adaptor 250 also can include a bracket 262 pivotally coupled to the attachment plate 258 (or to the foot 200). The bracket 262 can include a base 266 and a pair of arms 270 extending therefrom with distal ends pivotally coupled to the attachment plate 258 or foot 200. The cells 254 can be disposed between the first and second members, or the adaptor 250 and the attachment plate 258 or foot 200. Therefore, the adaptor 250 can be used with existing prosthetic feet to add cells. Again, the prosthetic foot can include a generator as described above and shown in FIG. 7.

Referring to FIG. 9b, a plurality of cells 260 can be disposed between first and second members 264 and 266 of a prosthetic foot. The cells can be positioned in for and aft locations with respect to a pivot point 270 to variably resist movement between the members 264 and 266 in the for and aft directions, or to variably resist plantar flexion and dorsal flexion. Similarly, the cells can be positioned on opposite lateral sides with respect to the pivot point 270 to variably resist movement between the members 264 and 266 in the side to side directions, or to variably resist inversion and eversion. Such a configuration can be applied to either of the prosthetic feet shown in FIGS. 8 and 9.

Figure 10:
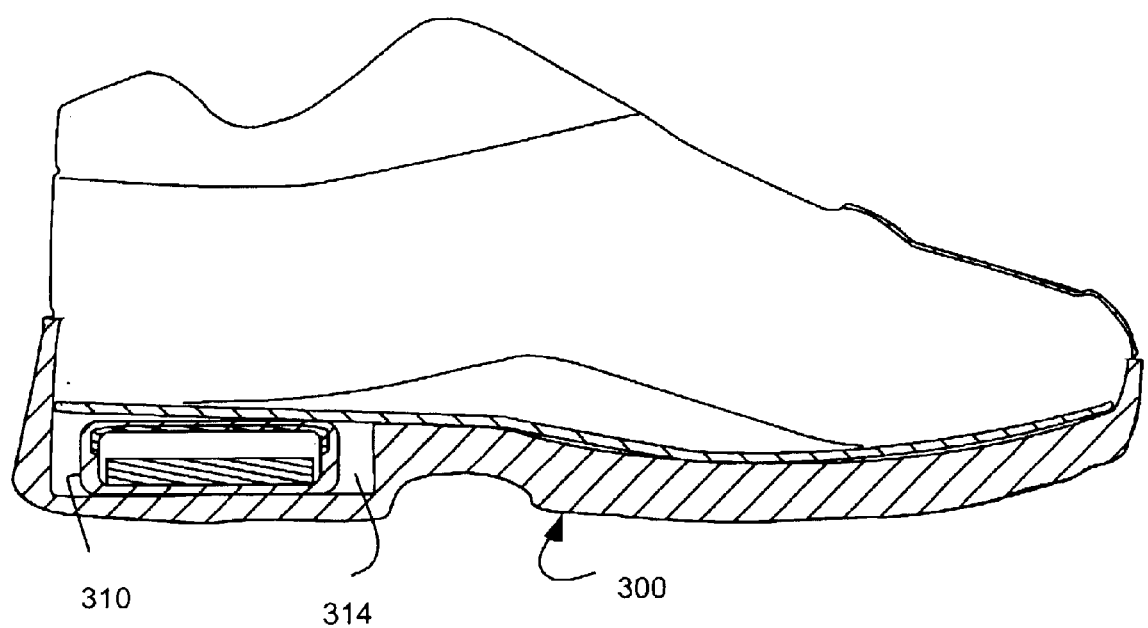
FIG. 10 is a cross-sectional side view of a shoe with a variable resistance cell in accordance with the present invention.

Referring to FIG. 10, a shoe 300 is shown with a variable resistance cell 310. The cell 310 can be positioned at a heel of the shoe, and can act as a cushion. A cavity 314 can be formed in the heel to receive the cell 310. The cell can be disposed between upper and lower surfaces of an outsole. A generator, as described above and shown in FIG. 7, can be included in the shoe and operatively coupled to the cell.

Figure 11:
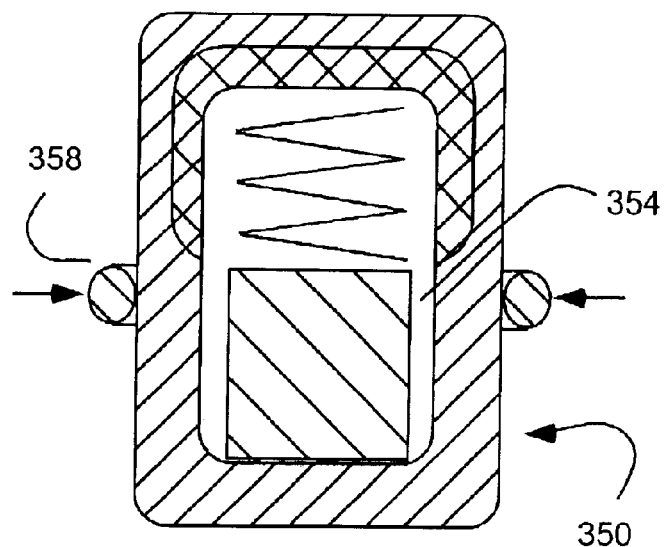
FIG. 11 is a cross-sectional side view of another variable resistance cell in accordance with an embodiment of the present invention, shown under a relatively larger load factor.
Figure 12:
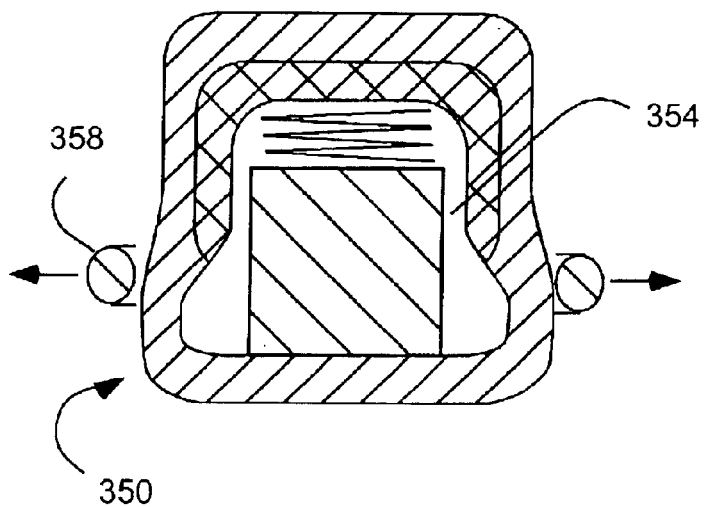
FIG. 12 is a cross-sectional side view of the variable resistance cell of FIG. 11, shown under a relatively smaller load factor.

Referring the FIGS. 11 and 12, another variable resistance cell 350 in accordance with the present invention that is similar in many respects to those described above. The cell 350 can include a variable orifice 354 that is variable in size and/or shape. An actuator 358 can be associated with the orifice 354 to vary the size of the orifice. For example, the actuator can surround the enclosure, and can constrict to reduce the size of the orifice, and can expand to increase the size of the orifice. Alternatively, a servo-valve can form the orifice, and can be disposed between the first and second chambers. The servo-valve can have an opening that varies in size. It will be understood that the cell with the variable orifice can be used with variable viscosity fluids described above, and other fluids that are not necessarily variable in their viscosity because the flow through the orifice can be controlled by the variable orifice.

The enclosure can include a bladder to contain the fluid. The block and cup, or magnets, can be movably disposed with respect to one another, with the magnets moving towards one another under the load factor.

A method for variably resisting a load factor in accordance with the present invention includes displacing a variable viscosity fluid through a variable resistance cell. As described above, the cell can include an enclosure with two chambers and an orifice positioned between the two chambers so that the variable viscosity fluid can flow between the two chambers through the orifice. The variable resistance load cell can be compressed by applying a load factor to the variable resistance cell. The viscosity of the fluid can be varied in response to the load factor by increasing the viscosity for a relatively larger load factor, and decreasing the viscosity for a relatively smaller load factor. In addition, the control electronics can be programmed to vary the viscosity of the fluid in response to the load factor, and a predetermined program It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. A variable resistance cell device configured to provide a variable resistance response to a load factor, the device comprising:
    a) an enclosure with first and second chambers;
    b) an orifice, operatively disposed between the first and second chambers, and sized to provide resistance against fluid flow therethrough;
    c) a variable viscosity fluid, disposed in the enclosure and displacable between the first and second chambers though the orifice in response to the load factor; and
    d) the variable viscosity fluid having a viscosity that is variable corresponding to the load factor to vary an ability of the variable viscosity fluid to flow through the orifice; and
    e) the enclosure being compressible between:
        1) a first position in response to a relatively larger load factor having a first larger dimension and in which a lesser amount of the variable viscosity fluid passes through the orifice into the second chamber; and
        2) a second position in response to a relatively smaller load factor having a second smaller dimension and in which a greater amount of the variable viscosity fluid passes through the orifice into the second chamber;
    f) a block, disposed in the enclosure, dividing the enclosure into the first and second chambers and forming the orifice between the block and the enclosure; and
    g) a cup, formed around the first chamber, to receive the block therein in the second position.

2. A device in accordance with claim 1, further comprising:
    a) a spring, coupled to the enclosure, and biasing the enclosure to the first position.

3. A device in accordance with claim 1, wherein the enclosure is resilient and biased to the first position.

4. A device in accordance with claim 1, wherein the enclosure is flexible.

5. A device in accordance with claim 4, wherein the enclosure flexes outwardly in the second position to form the second chamber.

6. A device in accordance with claim 1, wherein the enclosure includes a tubular sleeve.

7. A device in accordance with claim 1, further comprising:
    a) means for varying the viscosity of the variable viscosity fluid in response to the load factor.

8. A device in accordance with claim 1, wherein the load factor includes at least one load factor selected from the group consisting of: a load, a load rate, a load acceleration, a strain, a strain rate, a strain acceleration, a pressure, a pressure rate, a pressure acceleration, a deflection, a deflection rate, and a deflection acceleration.

9. A device in accordance with claim 1, wherein the variable viscosity fluid includes a shear stiffening material that increases in viscosity with an increase in the load factor applied to the shear stiffening material.

10. A device in accordance with claim 1, wherein the variable viscosity fluid includes at least one fluid selected from the group consisting of: a magneto rheologic fluid responsive to a magnetic field, and an electro rheologic fluid responsive to an electric field.

11. A device in accordance with claim 10, further comprising:
   a) a transducer to sense a load factor;
   b) a power source, coupled to the transducer;
   c) control electronics, coupled to the transducer and the variable viscosity fluid, to apply an electric or magnetic field in response to the load factor sensed by the transducer.

12. A device in accordance with claim 11, wherein the control electronics are programmable.

13. A device in accordance with claim 11, wherein the power source includes a generator.

14. A device in accordance with claim 1, wherein the block and the cup include a magnetic material.

15. A device in accordance with claim 1, wherein the orifice includes a variable orifice with a variable size.

16. A device in accordance with claim 1, wherein the enclosure is disposed between first and second members of a prosthetic foot.

17. A device in accordance with claim 1, wherein the enclosure is disposed in a shoe between upper and lower surfaces of an outsole.

18. A variable resistance cell device, comprising:
   a) a flexible tubular sleeve forming an enclosure;
   b) a block, disposed in the tubular sleeve, dividing the enclosure into first and second compartments with an orifice therebetween; and
   c) a variable viscosity fluid, disposed in the enclosure of the tubular sleeve, the variable viscosity fluid having a viscosity that is variable corresponding to the load factor to vary an ability of the variable viscosity fluid to flow through the orifice; and
   d) a cup, disposed in the tubular sleeve, to receive the block therein as the tubular sleeve is compressed.

19. A device in accordance with claim 18, further comprising:
   spring, disposed in the tubular sleeve, to bias the tubular sleeve to an expanded configuration.

20. A device in accordance with claim 18, wherein the flexible tubular sleeve is resilient and biased to an expanded configuration.

21. A device in accordance with claim 18, wherein the tubular sleeve flexes outwardly to form the second chamber.

22. A device in accordance with claim 18, further comprising:
   a) means for varying the viscosity of the variable viscosity fluid in response to a load factor.

23. A device in accordance with claim 22, wherein the load factor includes at least one load factor selected from the group consisting of: a load, a load rate, a load acceleration, a strain, a strain rate, a strain acceleration, a pressure, a pressure rate, a pressure acceleration, a deflection, a deflection rate, and a deflection acceleration.

24. A device in accordance with claim 18, wherein the variable viscosity fluid includes a shear stiffening material that increases in viscosity with an increase in a load factor applied to the shear stiffening material.

25. A device in accordance with claim 18, wherein the variable viscosity fluid includes at least one fluid selected from the group consisting of: a magneto rheologic fluid responsive to a magnetic field, and an electro rheologic fluid responsive to an electric field.

26. A device in accordance with claim 25, further comprising:
   a) a transducer to sense a load factor;
   b) a power source, coupled to the transducer;
   c) control electronics, coupled to the transducer and the variable viscosity fluid, to apply an electric or magnetic field in response to the load factor sensed by the transducer.

27. A device in accordance with claim 18, wherein the block and the cup include a magnetic material.

28. A device in accordance with claim 18, wherein the tubular sleeve is disposed between first and second members of a prosthetic foot.

29. A device in accordance with claim 18, wherein the tubular sleeve is disposed in a shoe between upper and lower surfaces of an outsole.

30. A variable resistance cell device, comprising:
   a) a flexible tubular sleeve, disposed between first and second members of a prosthetic foot, forming an enclosure;
   b) a block, disposed in the tubular sleeve, dividing the enclosure into first and second compartments with an orifice therebetween; and
   c) a variable viscosity fluid, disposed in the enclosure of the tubular sleeve, the variable viscosity fluid having a viscosity that is variable corresponding to the load factor to vary an ability of the variable viscosity fluid to flow through the orifice.

31. A device in accordance with claim 30, further comprising:
   a cup, disposed in the tubular sleeve, to receive the block therein as the tubular sleeve is compressed.

32. A device in accordance with claim 30, wherein the orifice includes a variable orifice with a variable size.

* * * * *